United States Patent
Arenshtam et al.

(10) Patent No.: US 9,005,452 B2
(45) Date of Patent: Apr. 14, 2015

(54) DEVICE FOR PURIFYING FLUID

(76) Inventors: Alex Arenshtam, Qiryat Gat (IL); Pinchas Maman, Jerusalem (IL)

(*) Notice: Subject to any disclaimer, the term of this patent is extended or adjusted under 35 U.S.C. 154(b) by 1025 days.

(21) Appl. No.: 12/972,690

(22) Filed: Dec. 20, 2010

(65) Prior Publication Data

US 2012/0000860 A1 Jan. 5, 2012

Related U.S. Application Data

(60) Provisional application No. 61/288,295, filed on Dec. 20, 2009.

(51) Int. Cl.
| | | |
|---|---|---|
| *B01D 35/00* | (2006.01) | |
| *A61L 2/10* | (2006.01) | |
| *A61L 9/20* | (2006.01) | |
| *C02F 1/32* | (2006.01) | |
| *C02F 1/72* | (2006.01) | |
| *C02F 103/00* | (2006.01) | |

(52) U.S. Cl.
CPC . *A61L 2/10* (2013.01); *A61L 9/205* (2013.01); *C02F 1/325* (2013.01); *C02F 1/725* (2013.01); *A61L 2209/16* (2013.01); *B01D 2257/404* (2013.01); *B01D 2257/406* (2013.01); *B01D 2257/502* (2013.01); *B01D 2258/01* (2013.01); *B01D 2258/0283* (2013.01); *B01D 2259/804* (2013.01); *C02F 2103/002* (2013.01); *C02F 2103/005* (2013.01); *C02F 2201/004* (2013.01); *C02F 2201/3223* (2013.01); *C02F 2305/10* (2013.01)

(58) Field of Classification Search
USPC ............... 210/748.01, 748.1, 748.11, 748.12, 210/748.13, 748.14, 749, 232, 763, 153, 210/157.15, 157.3; 422/20, 22, 24, 243, 422/186, 186.3; 250/324, 325, 200, 428, 250/432 R, 493.1, 494.1, 503.1, 504 R, 250/507.11; 403/1, 177; 96/224
See application file for complete search history.

(56) References Cited

U.S. PATENT DOCUMENTS

| | | | | |
|---|---|---|---|---|
| 5,933,702 A | * | 8/1999 | Goswami | 422/186.3 |
| 6,238,631 B1 | * | 5/2001 | Ogata et al. | 422/186.3 |
| 6,558,639 B1 | * | 5/2003 | Watanabe et al. | 422/186.3 |

* cited by examiner

*Primary Examiner* — Joseph Drodge
*Assistant Examiner* — Cameron J Allen
(74) *Attorney, Agent, or Firm* — The Law Office of Michael E. Kondoudis

(57) ABSTRACT

A device for purifying a fluid is disclosed. The aforesaid device comprises: (a) a passage adapted for conducting a flow of the fluid, said passage provided with input and output openings; (b) a plurality of elongate members coated with a titanium oxide disposed within the passage; (c) fastening means for mechanically fixating terminals of the elongate members within the passage; (d) at least one source of ultraviolet radiation adapted for illuminating the elongate members; (e) pumping means adapted for generating the fluid flow through the passage from the input opening to the output opening. The fastening means comprises at least two fasteners. Each fastener comprises two mutually orthogonal spaced apart pluralities of parallel rods. The rods are adapted for restricting lateral displacement of the elongate members.

26 Claims, 8 Drawing Sheets

SECTION A-A

DEVICE FOR PURIFYING FLUID

FIELD OF THE INVENTION

The present invention relates to a photo-induced catalytic fluid purifier, and, more specifically, to a fluid purifier provided with fastener of working elongate elements comprising two mutually orthogonal spaced apart pluralities of parallel rods.

BACKGROUND OF THE INVENTION

Fluid streams, such as water or air, often include contaminants like dissolved halogenated or organic compounds, volatile organic compounds, nitrogen oxides, inorganic gases like hydrogen cyanide, and microorganisms such as bacteria, viruses, molds, and fungi. Photocatalysts can be used to purify the fluid stream by converting these contaminants into less harmful substances or materials which may be more easily removed from the fluid stream.

The conversion of contaminants occurs when the fluid stream is brought in contact with a photocatalyst illuminated by a nearby light source. The photocatalyst is typically deposited on the surface of a support structure of some type to provide a stable photocatalytic surface and to ensure that the photocatalyst is not carried away by the fluid stream. Reactors employing these basic concepts have been developed.

To be effective, the contaminants must be brought into contact with the photocatalyst. The effectiveness of this process is measured by the mass transfer coefficient of the reactor which is the rate at which the contaminant is transported from the fluid stream to the photocatalytic surface. If the mass transfer system of the reactor is inadequate then conversion of contaminants will be diminished. Thus, an effective reactor design should provide for adequate mass transfer from the bulk fluid to the photocatalyst.

U.S. Pat. No. 6,558,639 ('639) discloses a purifier for purifying a fluid by eliminating contaminants from the fluid. The purifier includes a fluid passage, through which the fluid flows, formed by an ultraviolet ray transmitting material. A plurality of photocatalytic pipes are arranged in the fluid passage. Each of the photocatalytic pipes has an inner surface and an outer surface on which a thin film of a photocatalyst is applied. The photocatalytic thin film is excited by ultraviolet rays irradiated from a source located near the fluid passage. This oxidizes and decomposes the contaminants and purifies the fluid.

The elongate members 9 of '639 are packed into the outer pipe creating a problem of flow resistance. Additionally, the UV radiation achieves internal catalytic $TiO_2$ coating 9a through a number of outer $TiO_2$ coatings having sufficiently high reflective coefficient (0.5-0.9). Radiation intensity passed through at least to coatings 3a and 9b and striking upon the coating 9a is 0.25-0.01 of intensity that is incident on the surface 3. Thus, there is a unmet and long-felt need to provide a photo-catalytic decompounding device characterized by low flow resistance and high radiation efficiency.

SUMMARY OF THE INVENTION

It is hence one object of the invention to disclose a device for purifying a fluid. The aforesaid device comprises: (a) a passage adapted for conducting a flow of the fluid, the passage provided with input and output openings; (b) a plurality of elongate members coated with a titanium oxide disposed within the passage; (c) fastening means for mechanically fixating terminals of the elongate members within the passage; (d) at least one source of ultraviolet radiation adapted for illuminating the elongate members; (e) pumping means adapted for generating the fluid flow through the passage from the input opening to the output opening.

It is a core purpose of the invention to provide the fastening means comprising at least two fasteners. Each fastener comprises two mutually orthogonal spaced apart pluralities of parallel rods. The rods are adapted for restricting lateral displacement of the elongate members.

Another object of the invention is to disclose each elongate member provided with a groove configured for receiving side surface of corresponding rod in a close fitting manner so that the rod prevents longitudinal displacement of the elongate member.

A further object of the invention is to disclose each fastener comprising a frame mechanically framing the rods belonging thereto.

A further object of the invention is to disclose the fluid which is a gas.

A further object of the invention is to disclose the fluid which is a liquid.

A further object of the invention is to disclose the gas which is an exhaust gas.

A further object of the invention is to disclose the exhaust gas generated by an engine of an object selected from the group consisting of a motor vehicle, aerial vehicle, a marine vessel and any combination thereof.

A further object of the invention is to disclose the exhaust gas generated by a steam generator of a power plant.

A further object of the invention is to disclose the fluid contaminated with a contaminants selected from the group consisting of bacteria, viruses, mold, fungus, cleaning chemicals, paints, nitrogen oxides, solvents including chlorinated solvents, perfume, pesticides, alcohols, ammonia, carbon monoxide and any combination thereof.

A further object of the invention is to disclose the liquid which is potable water, grey water, black water and any combination thereof.

A further object of the invention is to disclose the liquid which is an industrial effluent.

A further object of the invention is to disclose ratio of a diameter d of the elongate member 40 to the side a which is equal to about 0.125.

A further object of the invention is to disclose quantity n of the elongate members 40 placed into the passage 15 which is given by the following expression $$n = \frac{0.2a^2}{d^2}.$$

A further object of the invention is to disclose the device providing a purified fluid characterized by a value of biochemical oxygen demand ranged between about M mg/L and about N mg/L.

A further object of the invention is to disclose the device providing a purified fluid characterized by a value of chemical oxygen demand ranged between about X mg/L and about Y mg/L.

A further object of the invention is to disclose a method of purifying a fluid. The aforesaid method comprises the steps of (a) providing a device for purifying a fluid; the device comprising: (i) a passage adapted for conducting a flow of the fluid, the passage provided with input and output openings; (ii) a plurality of elongate members coated with a titanium oxide disposed within the passage; (iii) fastening means for mechanically fixating terminals of the elongate members within the passage; (iv) at least one source of ultraviolet radiation adapted for illuminating the elongate members; (v) pumping means adapted for generating the fluid flow through the passage from the input opening to the output opening; (vi) fastening means comprises at least two fasteners, each fastener comprises two mutually orthogonal spaced apart pluralities of parallel rods; the rods are adapted for restricting lateral displacement of the elongate members; (b) generating the fluid flow through the passage from the input opening to the output opening; and (c) purifying the fluid by means of photo-induced catalytic degradation.

It is a core purpose of the invention to provide the fluid flow conducted through apertures between the spaced rods of the fasteners.

A further object of the invention is to disclose each elongate member provided with a groove configured for receiving side surface of corresponding rod in a close fitting manner so that the rod prevents longitudinal displacement of the elongate member.

A further object of the invention is to disclose the rods belonging to each fastener which are mechanically framed.

A further object of the invention is to disclose the fluid purified at said step of purifying said fluid by means of photo-induced catalytic degradation which is characterized by a value of biochemical oxygen demand ranged between about M mg/L and about N mg/L.

A further object of the invention is to disclose the fluid purified at said step of purifying said fluid by means of photo-induced catalytic degradation which is characterized by a value of chemical oxygen demand ranged between about X mg/L and about Y mg/L

BRIEF DESCRIPTION OF THE DRAWINGS

In order to understand the invention and to see how it may be implemented in practice, a plurality of embodiments is adapted to now be described, by way of non-limiting example only, with reference to the accompanying drawings, in which.

DETAILED DESCRIPTION OF THE INVENTION

The following description is provided, alongside all chapters of the present invention, so as to enable any person skilled in the art to make use of said invention and sets forth the best modes contemplated by the inventor of carrying out this invention. Various modifications, however, are adapted to remain apparent to those skilled in the art, since the generic principles of the present invention have been defined specifically to provide a device and a method for purifying a fluid.

An air purifier is a device which removes contaminants from the air. Air purifiers for residential use are commonly marketed as being particularly beneficial to allergy sufferers and asthmatics, and at reducing or eliminating second-hand tobacco smoke. Commercial grade air purifiers are manufactured as both a small stand-alone unit, and as larger units that can be affixed to an air handler unit (AHU) or to an HVAC unit found in the medical, industrial, and commercial industries.

Dust, pollen, pet dander, mold spores, and dust mite feces can act as allergens, triggering allergies in sensitive people. Smoke particles and volatile organic compounds (VOCs) can pose a risk to health. Exposure to various components such as VOCs increases the likelihood of experiencing symptoms of sick building syndrome. Additionally, with the advancement in technology, air purifiers are becoming increasingly capable of capturing a greater number of bacterial, virus, and DNA particulates. Air purifiers are used to reduce the concentration of these airborne contaminants and though very useful for people who suffer from allergies and asthma, technological and scientific studies are finding that poor air quality is more a contributing factor of some forms of cancer, respiratory illnesses, COPD, and other pulmonary infections and illnesses. They also reduce the need for frequent room and area cleaning. Air purifiers use a small amount of electrical energy, causing a small amount of expense and environmental effect.

Figure 1:
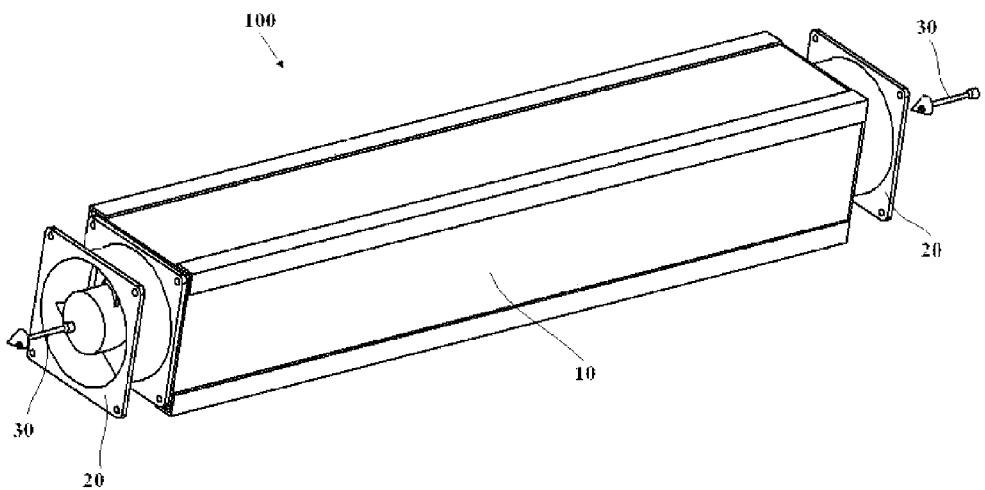
FIG. 1 is an exploded view of the purifying device.

Reference is now made to FIG. 1, showing an external exploded view of a purifying device 100. A housing 10 accommodates elongate members coated with $TiO_2$ which are illuminated by a lamp (not shown). Fans 20 force environmental air (fluid) to flow through the device 100 along a direction indicated by arrows 30.

Figure 2:
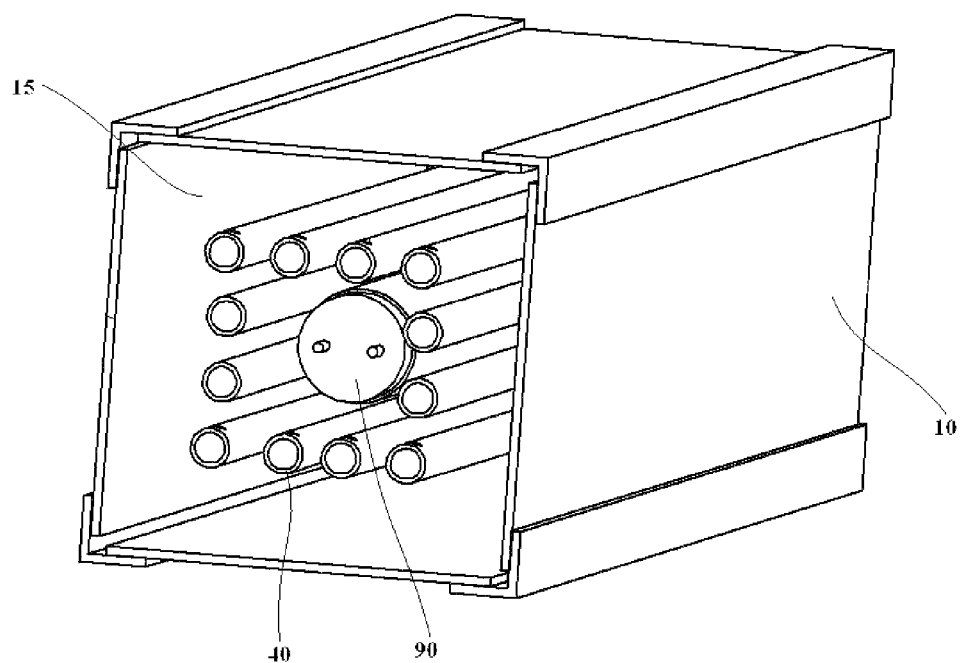
FIG. 2 is an interior arrangement of the purifying device.

Reference is now made to FIG. 2, presenting interior arrangement of the device 100. In a passage 15 defined by the housing 10, a lamp 90 illuminates elongated members 40 coated with $TiO_2$. Contaminants suspended in the pumped fluid undergo photo-induced catalytic degradation, so that contaminant particles are decomposed into less harmful or harmless compounds.

Figure 3:
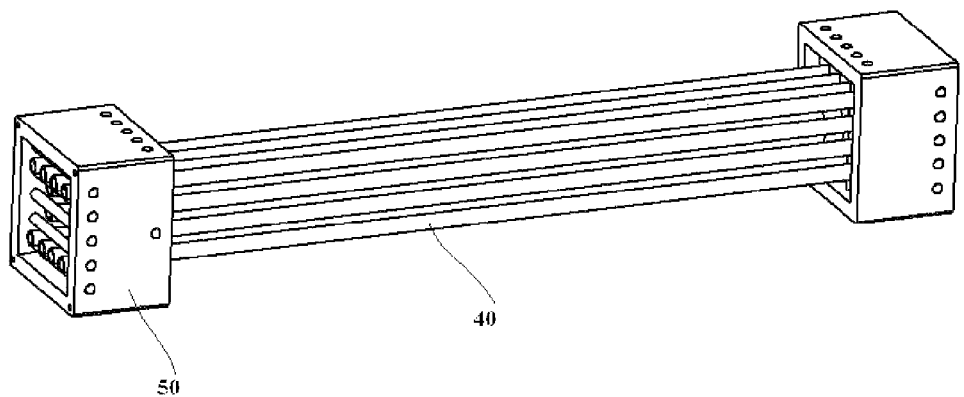
FIG. 3 is a schematic view of the plurality of the elongate members provided with fastener.

Reference is now made to FIG. 3, showing a plurality of elongate members 40 which are fastened by means of fasteners 50. The aforesaid fasteners provide longitudinal and lateral mechanical fixation so that the fluid to be purified is pumped along the elongate members 40 through the fasteners 50 with low flow resistance.

Figure 4:
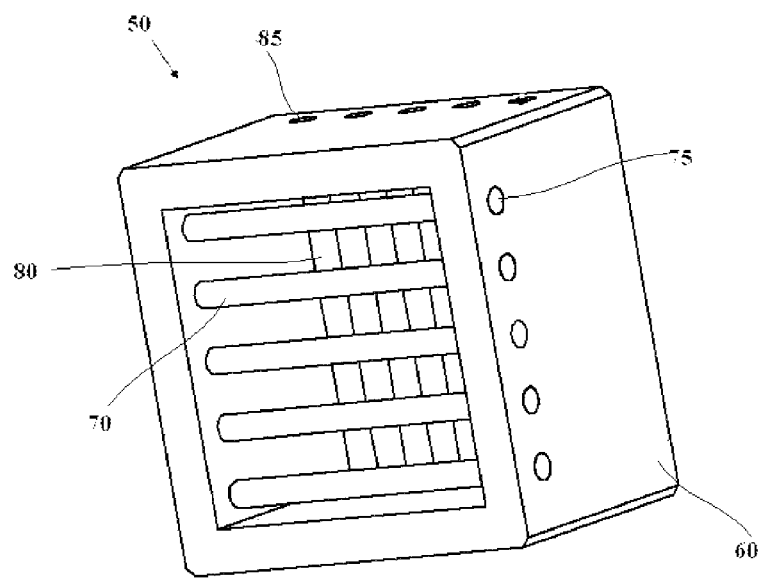
FIG. 4 is an isometric view of the fastener.
Figure 5:
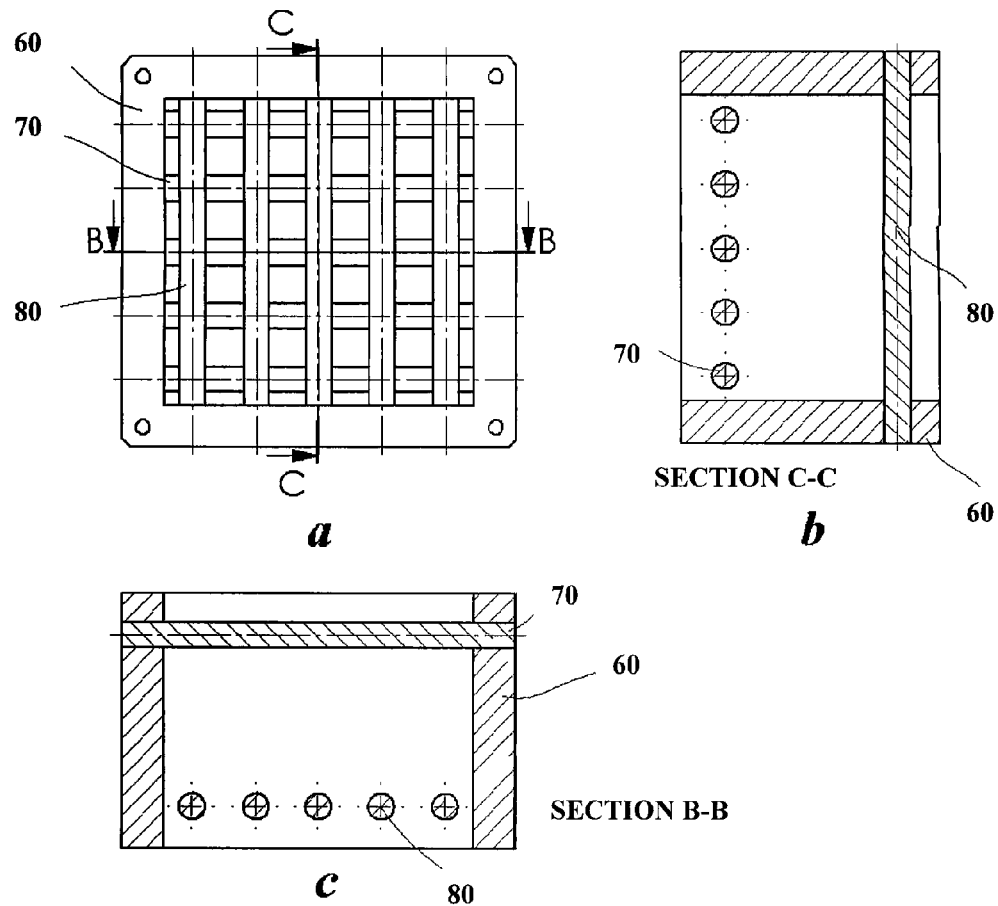
FIGS. 5*a-c* are a front view of the fastener and two cross-sectional views thereof.

Reference is now made to FIGS. 4 and 5*a-c*, presenting the fastener 50 which comprises a frame 60 and orthogonally related pluralities of rods 70 and 80. The rods belonging to each plurality are parallel inter se. The rods are framed into the frame 60. As seen in FIGS. 4 and 5, the rod pluralities are spaced apart and provide fluid flow with substantially low resistance.

Figure 6:
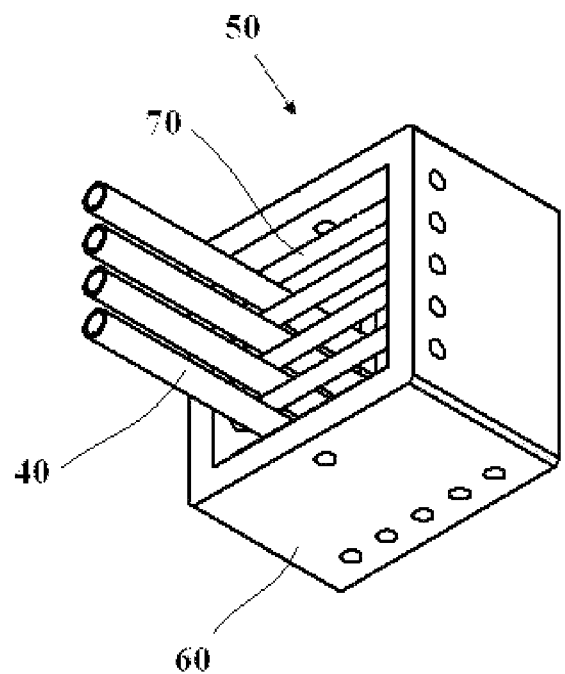
FIG. 6 is an isometric view of the fastener which receiving the plurality of the elongate members.
Figure 7:
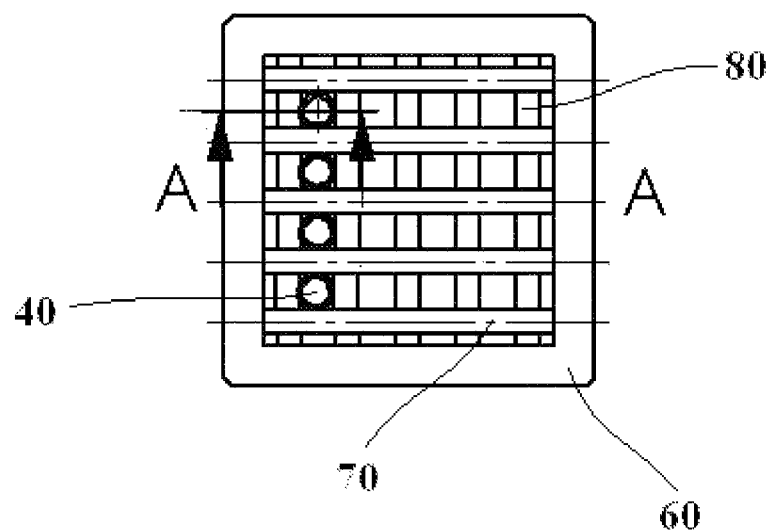
FIG. 7 is a front view of the fastener with the received elongate members.

Reference is now made to FIGS. 6 and 7, showing the fastener 50 which receives the elongate members 40. The rods 70 restrict the lateral displacement of the elongate members 40 in a vertical direction, while the rods 80 restrict displacement in a horizontal direction whereby fluid flow with substantially low resistance is provided.

Figure 8:
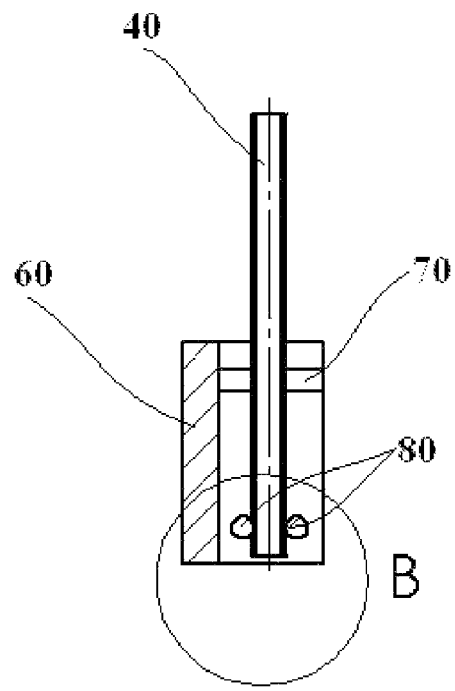
FIG. 8 is a cross-sectional view A-A of FIG. 10.

Reference is now made to FIG. 8, presenting a cross-sectional view of the elongate member 40 held in place or fastened by two rods 80 restricting lateral displacement of the elongate member 40 in the plane of FIG. 8. The rods 70 restrict lateral displacement of the elongate member 40 in a direction perpendicular to the figure plane.

Figure 9:
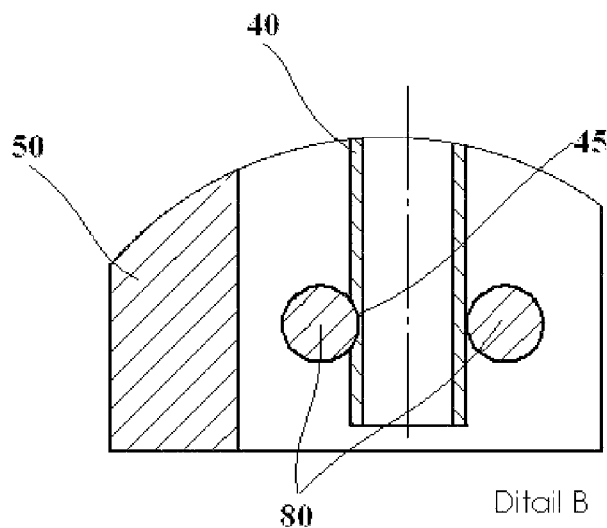
FIG. 9 is a detail B of FIG. 11.
Figure 10:
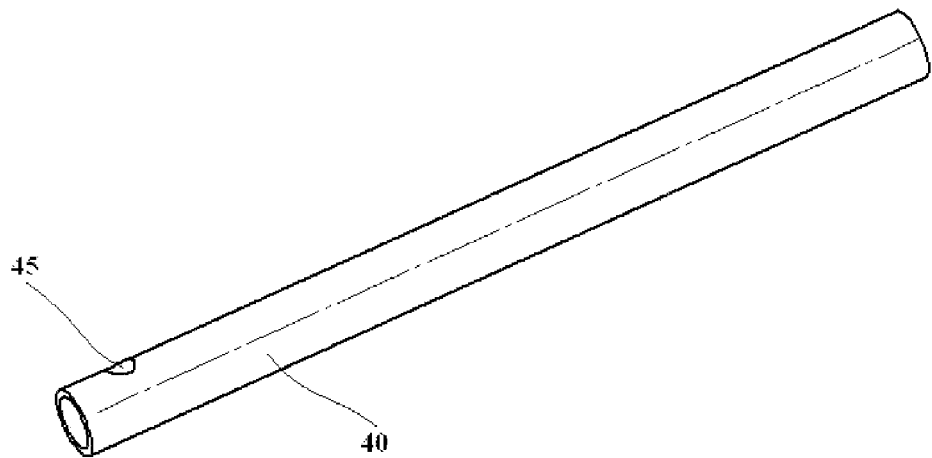
FIG. 10 is an isometric view of elongate member.

Reference is mow made to FIGS. 9 and 10, showing an embodiment of the current invention providing restriction of longitudinal displacement of the elongate members 40. As seen in the FIGS. 9 and 10, the elongate member 40 is provided with a grove 45 configured to receive a side surface of the rod 80 so that the rod 80 fixates the longitudinal member 40 and prevents it from longitudinal displacement.

Figure 11:
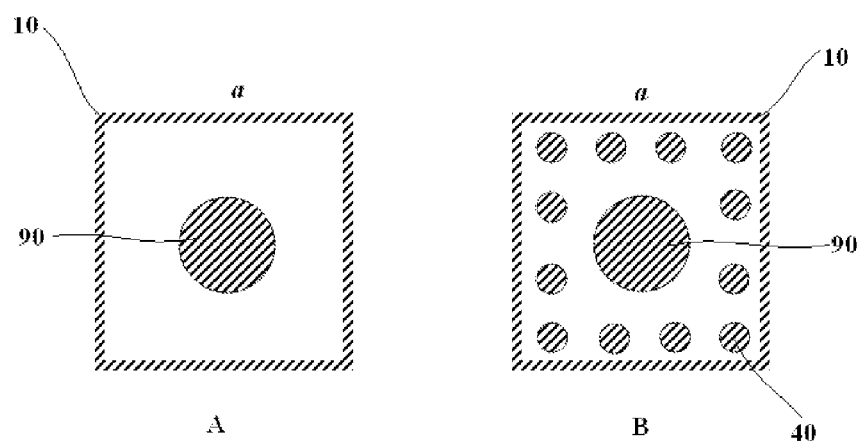
FIG. 11*a* is a cross-sectional view of the prior art the passage arrangement.
FIG. 11*b* is a cross-sectional view of the prior art the passage arrangement of the current invention.

Reference is now made to FIG. 11a and 11b, presenting cross-sectional views of the air passages belonging to the purifying device available in the market at the moment (FIG. 11a) and the purifying device according to the current invention (FIG. 11b).

To estimate efficiency of the proposed invention in comparison with commercially successful technical solutions which are available in the market let us admit the following assumptions. Most purifying devices are configured as a passage accommodating a UV lamp and conducting a fluid flow. On the presumption that cross-sectional dimensions of compared purifying devices are equal to each other along the whole length of the passages, it is reasonable to compare values of cross-sectional perimeters of the surfaces coated with titanium dioxide. Specifically, for the sake of simplicity, we assume that the cross section of the compared passages 10 is a square with a side a.

In the available purifying device, a perimeter of the square cross section is 4a.

On the basis of experimental investigations, it is shown that an optimal ratio of the diameter d of the elongate member 40 to the side a is d/a=0.125 and optimal quantity of the elongate members 40 placed into the passage is given by the following expression $$n = \frac{0.2a^2}{d^2}.$$

The aforesaid perimeter ratio is $$J = \frac{4a + 0.2\pi d \frac{a^2}{d^2}}{4a} = \frac{4a + 0.2 \cdot 3.14 \cdot 0.125a \cdot \frac{a^2}{(0.125a)^2}}{4a} = 2.2$$

Thus, the proposed purifying device is 2.2 time effective in comparison with the device of identical dimensions available in the market.

Concerning flow resistance of the proposed device, the performed calculations by means of the Hagen-Poiseuille equation $$\Delta P = \frac{128\mu L Q}{\pi d^4},$$

where $\Delta P$ is the pressure drop at an output of the device in comparison with input pressure, L is the length of the passage, $\mu$ is the fluid dynamic viscosity, Q is the volumetric flow rate, d is the diameter of the passage, have shown that an expected value of the flow resistance provided by the proposed purifying device is about a half of the flow resistance of a passage of equivalent diameter and length.

Figure 12:
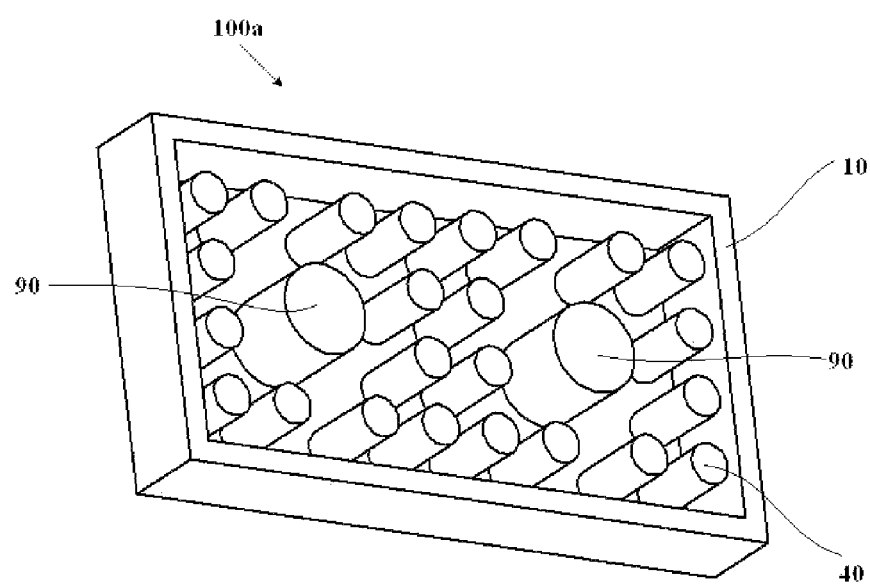
FIG. 12 is an internal view of the purifier embodiment provided with two lamps.

Reference is now made to FIG. 12, presenting an embodiment of the current invention characterized by the higher efficiency. The air purifier 100a is provided with two UV lamp 90 which illuminates the elongate members 40 accommodated in the housing 10. An optimal arrangement comprises 24 elongate members 40. Optimal geometric parameters are following: a length of the lamps and elongate members is 2 m and more; a diameter of the elongate members is 20 mm and more.

The invention claimed is:

1. A device 100 for purifying a fluid; said device comprising:
   (a) a passage 15 adapted for conducting a flow of said fluid, said passage 15 provided with input and output openings;
   (b) a plurality of elongate members 40 coated with a titanium oxide disposed within said passage;
   (c) fastening means for mechanically fixating said elongate members 40 within said passage 15;
   (d) at least one source of ultraviolet radiation 90 adapted for illuminating said elongate members 40;
   (e) a pump 20 adapted for generating said fluid flow through said passage from said input opening to said output opening;
   wherein said fastening means comprises at least two fasteners 50, each fastener 50 comprises two mutually orthogonal spaced apart pluralities of parallel rods 70 and 80; said rods 70 and 80 are adapted for restricting lateral displacement of said elongate members 40.

2. The device according to claim 1, wherein said fluid is a gas.

3. The device according to claim 2, wherein said gas is an exhaust gas.

4. The device according to claim 3, wherein said exhaust gas is generated by an engine of an object selected from the group consisting of a motor vehicle, aerial vehicle, a marine vessel and any combination thereof.

5. The device according to claim 2, wherein said fluid is contaminated with a contaminants selected from the group consisting of bacteria, viruses, mold, fungus, cleaning chemicals, paints, nitrogen oxides, solvents including chlorinated solvents, perfume, pesticides, alcohols, ammonia, carbon monoxide and any combination thereof.

6. The device according to claim 3, wherein said exhaust gas is generated by a steam generator of a power plant.

7. The device according to claim 1, wherein said fluid is a liquid.

8. The device according to claim 7, wherein said liquid is potable water, grey water, black water and any combination thereof.

9. The device according to claim 7, wherein said liquid is an industrial effluent.

10. The device according to claim 7, wherein said fluid is contaminated with a contaminants selected from the group consisting of bacteria, viruses, mold, fungus, cleaning chemicals, paints, nitrogen oxides, solvents including chlorinated solvents, perfume, pesticides, alcohols, ammonia, carbon monoxide and any combination thereof.

11. The device according to claim 1, wherein each elongate member 40 is provided with a groove 45 configured for receiving side surface of corresponding rod 80 in a close fitting manner so that said rod 80 prevents longitudinal displacement of said elongate member 40.

12. The device according to claim 1, wherein each fastener comprises a frame 60 mechanically framing said rods 70 and 80 belonging thereto.

13. The device according to claim 1, wherein a ratio of a diameter d of the elongate member 40 to a side a is equal to about 0.125.

14. The device according to claim 1, wherein quantity n of the elongate members 40 placed into the passage 15 is given by the following expression $$n = \frac{0.2a^2}{d^2},$$

where a is the side of said passage 15 and d is the diameter of said elongate member 40.

15. A method of purifying a fluid; said method comprising the steps of
    (a) providing a device 100 for purifying a fluid; said device comprising:
        i. a passage 15 adapted for conducting a flow of said fluid, said passage 15 provided with input and output openings;
        ii. a plurality of elongate members 40 coated with a titanium oxide disposed within said passage 15;
        iii. fastening means for mechanically fixating terminals of said elongate members 40 within said passage 15;
        iv. at least one source 90 of ultraviolet radiation adapted for illuminating said elongate members 40;
        v. pump 20 adapted for generating said fluid flow through said passage 15 from said input opening to said output opening;
        vi. fastening means comprises at least two fasteners 50, each fastener 50 comprises two mutually orthogonal spaced apart pluralities of parallel rods 70 and 80; said rods 70 and 80 are adapted for restricting lateral displacement of said elongate members 40;
    (b) generating said fluid flow through said passage 15 from said input opening to said output opening; and
    (c) purifying said fluid by means of photo-induced catalytic degradation;
    wherein said fluid flow is conducted through apertures between said spaced rods 70 and 80 of said fasteners 50.

16. The method according to claim 15, wherein said step of purifying said fluid comprises a sub-step of purifying a gas.

17. The method according to claim 16, wherein said sub-step of purifying a gas comprises purifying an exhaust gas.

18. The method according to claim 17, wherein said exhaust gas is generated by an engine of an object selected from the group consisting of a motor vehicle, aerial vehicle, a marine vessel and any combination thereof.

19. The method according to claim 18, wherein said exhaust gas is generated by a steam generator of a power plant.

20. The method according to claim 16, wherein said fluid is contaminated with a contaminants selected from the group consisting of bacteria, viruses, mold, fungus, cleaning chemicals, paints, nitrogen oxides, solvents including chlorinated solvents, perfume, pesticides, alcohols, ammonia, carbon monoxide and any combination thereof.

21. The method according to claim 15, wherein said step of purifying said fluid comprises a sub-step of purifying a liquid.

22. The method according to claim 21, wherein said sub-step of said liquid comprises purifying potable water, grey water, black water and any combination thereof.

23. The method according to claim 21, wherein said fluid is contaminated with a contaminants selected from the group consisting of bacteria, viruses, mold, fungus, cleaning chemicals, paints, nitrogen oxides, solvents including chlorinated solvents, perfume, pesticides, alcohols, ammonia, carbon monoxide and any combination thereof.

24. The method according to claim 21, wherein said sub-step of said liquid comprises purifying an industrial effluent.

25. The method according to claim 15, wherein said rod 80 prevents longitudinal displacement of said elongate member 40.

26. The method according to claim 15, wherein said rods belonging to each fastener 50 are mechanically framed.

* * * * *